US009314545B2

(12) United States Patent
Tofighi et al.

(10) Patent No.: US 9,314,545 B2
(45) Date of Patent: Apr. 19, 2016

(54) MINIMALLY INVASIVE TREATMENT OF VERTEBRA (MITV) USING A CALCIUM PHOSPHATE COMBINATION BONE CEMENT

(75) Inventors: Aliassghar N. Tofighi, Waltham, MA (US); Aron D. Rosenberg, Brighton, MA (US); Tak Lung Chang, Boxborough, MA (US); Michael Strunk, Woburn, MA (US)

(73) Assignee: LIFE SCIENCE ENTERPRISES, INC., Waltham, MA (US)

( * ) Notice: Subject to any disclaimer, the term of this patent is extended or adjusted under 35 U.S.C. 154(b) by 1248 days.

(21) Appl. No.: 12/937,944

(22) PCT Filed: Apr. 15, 2009

(86) PCT No.: PCT/US2009/040680
§ 371 (c)(1),
(2), (4) Date: May 31, 2011

(87) PCT Pub. No.: WO2009/129316
PCT Pub. Date: Oct. 22, 2009

(65) Prior Publication Data
US 2011/0224675 A1  Sep. 15, 2011

Related U.S. Application Data

(60) Provisional application No. 61/045,181, filed on Apr. 15, 2008.

(51) Int. Cl.
*A61B 17/88* (2006.01)
*A61L 24/02* (2006.01)
(Continued)

(52) U.S. Cl.
CPC .............. *A61L 24/02* (2013.01); *A61B 17/8811* (2013.01); *A61L 24/0015* (2013.01); *A61L 24/0036* (2013.01); *A61L 24/0042* (2013.01);
(Continued)

(58) Field of Classification Search
CPC ............... A61B 17/88; A61B 17/8802; A61B 17/8805; A61B 17/8811; A61B 17/8825
USPC ......... 606/86 R, 92–94; 106/35; 423/308–310
See application file for complete search history.

(56) References Cited

U.S. PATENT DOCUMENTS 5,508,342 A * 4/1996 Antonucci et al. ............. 524/788
5,650,108 A * 7/1997 Nies et al. ...................... 264/122
(Continued)

FOREIGN PATENT DOCUMENTS

JP    2001502215 A    2/2001
WO   WO-98/16268 A2   4/1998
(Continued)

OTHER PUBLICATIONS

International Search Report for PCT/US2009/040680, mailed Nov. 19, 2009.
(Continued)

*Primary Examiner* — Anu Ramana
(74) *Attorney, Agent, or Firm* — Clark & Elbing LLP

(57) ABSTRACT

Featured are a biocompatible, injectable, self-setting, cohesive, bone-bonding and remodeling calcium phosphate composite material and its use in methods of repairing defective bone, e.g., in vertebroplasty augmentation and kyphoplasty.

16 Claims, 3 Drawing Sheets

(51) Int. Cl.
*A61L 24/00* (2006.01)
*A61L 27/12* (2006.01)
*A61L 27/46* (2006.01)
*A61L 27/50* (2006.01)

(52) U.S. Cl.
CPC ......... *A61L24/0063* (2013.01); *A61L 24/0084* (2013.01); *A61L 27/12* (2013.01); *A61L 27/46* (2013.01); *A61L 27/50* (2013.01); *A61L 2300/44* (2013.01); *A61L 2400/06* (2013.01); *A61L 2400/12* (2013.01); *A61L 2430/02* (2013.01); *A61L 2430/38* (2013.01)

(56) References Cited

U.S. PATENT DOCUMENTS

| | | | |
|---|---|---|---|
| 6,071,982 | A | 6/2000 | Wise et al. |
| 6,132,463 | A | 10/2000 | Lee et al. |
| 6,461,631 | B1 | 10/2002 | Dunn et al. |
| 6,730,156 | B1* | 5/2004 | Windisch et al. ............... 106/35 |
| 6,749,595 | B1* | 6/2004 | Murphy ........................ 604/500 |
| 7,942,961 | B2* | 5/2011 | Asgary ........................... 106/35 |
| 2002/0137812 | A1 | 9/2002 | Chow et al. |
| 2003/0120351 | A1 | 6/2003 | Tofighi et al. |
| 2005/0257714 | A1* | 11/2005 | Constantz et al. ............. 106/35 |
| 2007/0032568 | A1 | 2/2007 | Lin et al. |
| 2007/0098811 | A1 | 5/2007 | Lu et al. |
| 2007/0128245 | A1* | 6/2007 | Rosenberg et al. ........... 424/423 |
| 2008/0028992 | A1 | 2/2008 | Lee et al. |

FOREIGN PATENT DOCUMENTS

| | | |
|---|---|---|
| WO | WO-2007/067561 A2 | 6/2007 |
| WO | WO-2009/032173 A1 | 3/2009 |

OTHER PUBLICATIONS

International Preliminary Report on Patentability for PCT/US2009/040680, mailed Oct. 19, 2010.

Yang et al. "Effect of tricalcium phosphate, hydroxyethyl methacrylate, and ethylene glycol dimethacrylate on the mechanical properties of acrylic bone cement," Die Angewandte Makromolekulare Chemie. 245(4258):49-62 (1997).

Communication pursuant to Article 94(3) EPC for European Application No. 09731897.6 dated May 26, 2014 (4 pages).

Office Action in Chinese Application No. 200980122023.7 dated May 29, 2014 (with English translation) (15 pages).

Office Action for CN200980122023.7, dated Mar. 5, 2013 (8 pages).

English Translation of Notice of Reasons for Rejection in Japanese Patent Application No. 2011-505170, dated Nov. 6, 2013 (2 pages).

English Translation of Second Office Action in Chinese Patent Application No. 200980122023.7, mailed Nov. 13, 2013 (9 pages).

Extended European Search Report for European Patent Application No. 09731897.6, dated Aug. 22, 2013 (5 pages).

Patent Examination Report No. 2 for Australian Patent Application No. 2009236216, dated Sep. 16, 2014 (5 pages).

Patent Examination Report No. 3 for Australian Patent Application No. 2009236216, dated Dec. 12, 2014 (4 pages).

Farlay et al., "Mineral maturity and crystallinity index are distinct characteristics of bone mineral," J Bone Miner Metab. 28(4):433-45 (2010).

Office Action for Canadian Patent Application No. 2,721,608, dated Jun. 9, 2015 (6 pages).

Notice for Reasons of Rejection and English Translation for Japanese Patent Application No. 2011-505170, dated Jun. 17, 2015 (7 pages).

\* cited by examiner

MINIMALLY INVASIVE TREATMENT OF VERTEBRA (MITV) USING A CALCIUM PHOSPHATE COMBINATION BONE CEMENT

CROSS-REFERENCE TO RELATED APPLICATIONS

This application claims priority under 35 U.S.C. §371 from international application PCT/US2009/040680, filed Apr. 15, 2009, which claims benefit of U.S. Provisional Application No. 61/045,181, filed Apr. 15, 2008.

BACKGROUND OF THE INVENTION

Naturally occurring bone is contains about 70% mineral (nanometer-sized calcium deficiency hydroxyapatite) and about 30% organic matrix (collagen, proteins etc.). Bone loss occurs as results of increased bone destruction (resorption by osteoclastic activity) relative to bone formation (by aging or disease). Both bone resorption and formation occur continuously in the skeleton as part of normal skeletal function. During this process packs of bone are being destroyed and rebuilt in a process called remodeling.

Osteoporosis is a disease characterized by low bone mass leading to an increased frequency of low energy fractures. It is known that osteoporosis is a condition that features loss of the normal density of bone and fragile bone. It leads to literally abnormally porous bone that is more compressible (e.g., spongy) than dense (e.g., brick). This disorder of the skeleton weakens the bone, which leads to an increase in the risk of breaking bones (bone fracture).

Bones that are affected by osteoporosis can fracture with only a minor fall or injury that normally would not cause a bone fracture. The fracture can be in the form of cracking (as in a hip fracture), or collapsing (as in a compression fracture of the vertebrae of the spine). The spine, hips, and wrists are common areas of osteoporosis-related bone fractures, although osteoporosis-related fractures can also occur in almost any skeletal bone area.

Among fractures encountered in osteoporosis, vertebral fractures must be taken into account because they are frequent (about 16% of postmenopausal women) and lead to back pain, disability and decreased height.

Bisphosphonates, which are analogues of naturally occurring pyrophosphate that contain a carbon instead of an oxygen atom, are widely used in the treatment of osteoporosis in order to inhibit osteoclastic bone resorption. Bisphosphonates have been observed to preferentially bind to bone mineral in areas that are actively undergoing remodeling. After desorption in bone, bisphosphonates are liberated again only when the bone is resorbed (by osteoclasts). The most common adverse event with bisphosphonate treatment is gastrointestinal disturbance, including, e.g., pain, diarrhea, and abdominal discomfort. Given that treatment for osteoporosis is typically long term, compliance and tolerability (without side effect) are important.

Despite the fact that traditional approaches (mostly based on non-surgical therapies as a preventive measure) have been shown to be ineffective in alleviating pain and correcting spinal deformity, the minimally invasive treatment of vertebral compression fracture (VCF) remains under-developed. Currently, vertebroplasty is performed by percutaneously injecting (by minimally invasive surgery (MIS)) a bone substitute material (BSM) into the vertebral bodies under fluoroscopic and/or computed tomography guidance. A related treatment, kyphoplasty, includes an attempt to expand the vertebra with an inflatable balloon prior to the injection of a BSM. Kyphoplasty is an effective treatment for painful osteoporotic compression fractures, however, patients who undergo kyphoplasty procedure should be informed of the significant risk of adjacent-level fractures over the next 60 days. The reason for this association is unclear, but may occur because cement augmentation at one vertebral level places further stress on adjacent levels.

Typically, a MIS technique allows for the same outcomes as conventional (open) surgery, but with additional benefits that include, e.g., the avoidance of open invasive surgery in favor of closed (tiny incision) or local surgery, a reduction in surgical complications (muscle stripping, blood loss, etc.), a reduction in operative trauma (by soft tissue preservation) with less postoperative pain, a reduction in patient hospitalization time and, consequently, a significant reduction in costs, an increase in the speed of functional return to daily activities, a shorter recovery time (a few months instead of a year), and a few cosmetically tiny scars rather than one large scar.

There are an estimated 800,000 vertebral fractures from osteoporosis every year according to the U.S. National Osteoporosis Foundation, and about 200,000 of these are treated surgically. The vertebrae compression fracture market is estimated at $160 million (in 2007) with the potential to reach $750 million as surgery continues to grow as the standard of care for the condition. In 2004, the global market for minimally invasive VCF treatments, including Kyphoplasty and Percutaneous Vertebroplasty (PV), was valued at more than $250 million.

The current product in today's market used for vertebroplasty indication is a decades-old, non-bioresorbable, and non-remodeling polymethylmethacrylate (PMMA) cement, which is injected in the vertebral body for pain relief and to strengthen weakened vertebral bone. PMMA cement is remarkably strong and does not deteriorate over time, yet it also does not integrate into bone. Moreover, the high compression strength of PMMA can cause adjacent vertebral body fractures by exerting high non-compliant forces on the adjacent occurring adjacent fractures.

In 2007, Health Canada issued information related to serious complications associated with the use of PMMA cement in vertebroplasty and kyphoplasty procedures. Among these complications are the following: death due to sudden blood pressure drop that may be related to the release of the PMMA monomer (leaching effect) into the vascular system, PMMA extravasations into the spinal canal leading to neurologic deficit, with compression of the spinal cord and/or nerve roots, new fractures, usually of adjacent non-augmented vertebrae, and pulmonary embolism due to PMMA.

Unlike PMMA, calcium phosphate cement (CPC), when delivered into the bone, is acted upon by osteoblasts and osteoclasts in the residual trabecular bone and can be remodeled into bone. With its lower compressive strength, CPC also causes less stiffness of the vertebral body. CPC can also integrate into the trabecular bone structure and can promote bone restoration.

There exists a need for compositions that can be used in kyphoplasty and vertebroplasty applications that avoid the complications associated with PMMA cement compositions.

SUMMARY OF THE INVENTION

The invention features a biocompatible, injectable, self-setting, cohesive, bone-bonding and remodeling calcium phosphate (CaP) composite material and its use in methods for vertebroplasty augmentation. In preferred embodiments, the CaP material is a nanocrystalline apatite (NCA) or a nano-low crystalline apatite (NLCA), which can be synthesized using, e.g., a low temperature double decomposition technique or a high energy grinding technique. The CaP material of the present invention may also include polymers or other chemical bonding agents, such as polylactic acid (PLA) and hydroxyethyl methacrylate (HEMA) monomers. Unlike PMMA-containing cements, the CaP materials of the present invention can be remodeled in vivo and do not contain volatile monomers that can be "leached" into the body of a patient.

In a first aspect, the invention features a method for performing vertebroplasty on a vertebral body by injecting (e.g., through a 16 gauge needle or less, e.g., an 11 gauge needle) a flowable bone cement into at least one vertebral body (e.g., by directly injecting into the vertebral body or by injecting into the vertebral body after creating a cavity) of a mammal (e.g., a human or a non-human mammal) and allowing the flowable bone cement to harden. The flowable bone cement includes a calcium phosphate material (e.g., a nanocrystalline apatitic calcium phosphate, such as a NCA and a NLCA), a radio-opaque agent, and a pharmaceutically acceptable fluid in an amount sufficient to produce the flowable bone cement. The calcium phosphate can be selected from amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof. When hardened, the flowable bone cement has a compressive strength of 1 mPa or greater and is resorbable in vivo. In an embodiment, the flowable bone cement further includes one or more of at least one agent that promotes bone growth or inhibits bone resorption, demineralized bone matrix, and one or more crystal growth inhibitors, or is formed using one or more of benzoyl peroxide powder, hydroxyethyl methacrylate (HEMA), and dimethyl-p-toluidine. In other embodiments, the calcium phosphate material is chemically bonded using a polymer (e.g., polylactic acid) or other chemical bonding agent (e.g., HEMA).

In other embodiments, the flowable bone cement further includes a cohesiveness agent, an osteogenic agent, or a medicinal agent. The cohesiveness agent can be selected from the group consisting of:

a) one or more polymers selected from polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly (vinyl alcohol), poly(vinylpyrrolidone), poly (ethyloxazoline), poly(ethylene oxide)-co-poly(propylene oxide) block copolymers, poly(ethylene terephthalate)polyamide, and copolymers thereof;

b) a homo- or co-polymer having one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone);

c) a polyphenolic complexing agent selected from gallotannins, ellagitannins, taragallotannins, caffetannins, proanthocyanidins, catechin, epicatechin, chlorogenic acid, and arbutin; or d) an agent selected from alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, a glucosamine, a proteoglycan, a starch, lactic acid, a pluronic, sodium glycerophosphate, collagen, glycogen, a keratin, silk, and mixtures thereof.

In other embodiments of the first aspect of the invention, the osteogenic agent is selected from the group consisting of transforming growth factors-beta (TGF-$\beta$), activins, inhibins, and bone morphogenetic proteins (BMPs), while the medicinal agent is selected from the group consisting of antibiotics, enzyme inhibitors, antihistamines, anti-inflammatory agents, muscle relaxants, anti-spasmodics, analgesics, prostaglandins, anti-depressants, trophic factors, and hormones.

In yet other embodiments of the first aspect of the invention, the pharmaceutically acceptable fluid is selected from water, saline, a phosphate buffer, a biological fluid, in particular, blood or a fluid that includes blood components, and glycerol. The method also includes injecting the flowable bone cement into two or more vertebral bodies. In addition, the vertebral body may be fractured or osteoporotic bone. In other embodiments, the calcium phosphate material has crystals within the range of 30-80 nm (e.g., 30-50 nm) or has a crystallinity index value of less than 60% (preferably less than 50%, and more preferably less than 40%) relative to hydroxyapatite.

In other embodiments, the method involves a minimally invasive surgery, which entails the formation of one or more tiny (less than 2 inches, more preferably less than 1 inch) incisions that allow insertion of a syringe needle through the incision to the site of the vertebral body. The flowable bone cement can be administered through a syringe, which eliminates the need for a large entry point into the patient. The method reduces surgical complications (e.g., muscle stripping, blood loss etc.), reduces operative trauma (e.g., by preserving soft tissue) and postoperative pain, reduces patient hospitalization time, increases the speed of functional recovery and decreases recovery time (e.g., to a few months rather than a year or more), and leaves a few tiny scars instead of one large scar.

A second aspect of the invention features a flowable bone cement that includes a calcium phosphate material (e.g., a nanocrystalline apatite (NCA) or a nano-low crystalline apatite (NLCA), which can be synthesized using, e.g., a low temperature double decomposition technique or a high energy grinding technique) and a pharmaceutically acceptable fluid (e.g., water, saline, a phosphate buffer, a biological fluid, in particular, blood or a fluid that includes blood components, and glycerol), wherein said flowable bone cement is injectable (e.g., through a needle having a size of at least 16 gauge or less (e.g., 11 gauge or less)) and hardens in less than 1 hour at 37° C. and, after hardening, has a compressive strength of 1 mPa or greater and is resorbable in vivo. In an embodiment, the flowable bone cement includes a radio-opaque agent or a supplemental agent (e.g., a cohesiveness agent, an osteogenic agent, and a medicinal agent). In other embodiments, the calcium phosphate material is chemically bonded using a polymer (e.g., polylactic acid) or other chemical bonding agent (e.g., HEMA). In other embodiments, the calcium phosphate is selected from amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof. In yet other embodiments, the flowable bone cement includes a pore-forming agent, e.g., an effervescent agent, at least one agent that promotes bone growth or inhibits bone resorption, demineralized bone matrix, or one or more crystal growth inhibitors, or is formed by using benzoyl peroxide powder or hydroxyethyl methacrylate (HEMA) and dimethyl-p-toluidine.

In yet other embodiments of the second aspect of the invention, the calcium phosphate has crystals within the range of 30-80 nm (e.g., 30-50 nm) or has a crystallinity index value of less than 60% (preferably less than 50% and more preferably less than 40%) relative to hydroxyapatite.

A third aspect of the invention features a kit that includes the flowable bone cement of the second aspect of the invention and a syringe for delivery of the flowable bone cement.

A fourth aspect of the invention features a method for making nanocrystalline apatite (NCA) and nano-low crystalline apatite (NLCA) CaP materials using a low temperature double decomposition technique or a high energy grinding technique and adding a cohesiveness agent or by chemically bonding the CaP material using a polymer (e.g., polylactic acid) or, e.g., HEMA, to form a flowable bone cement that is capable of hardening at 37° C. in less than 2 hours, preferably less than 1 hour, more preferably less than 30 minutes, and most preferably between 10 and 30 minutes and that, prior to hardening, can be injected using a 16 gauge or less needle (e.g., an 11 gauge needle). Once hardened, the material has a compressive strength of 1 mPa or greater (e.g., a compressive strength in the range of about 1 MPa to about 150 MPa (e.g., 2, 10, 20, 30, 40, 50, 60, 70, 80, 90, 100, or 120 MPa or greater)).

As used herein, the term "about" means±10% of the recited value.

As used herein, a "biocompatible" substance is one that does not produce an unacceptable or undesirable physiological response, e.g., an immune response, in the recipient.

As used herein and applied to a CaP composite of the invention, the term "cohesiveness" means the ability of CaP composite to maintain its shape without loss of mass. A composite is deemed cohesive if greater than 90% of its initial mass and volume are retained within its initial shape dimension following incubation in an aqueous environment for at least 10 minutes.

By "bioresorabable" is meant capable of being degraded or metabolized in vivo by the body and resorbed and/or eliminated through normal excretory routes by the body. Such metabolites or break-down products should be substantially non-toxic to the body.

As used herein, a "cohesiveness agent" means an additive that, when included in a CaP composite of the invention, improves the ability of the CaP composite to maintain its cohesiveness. Preferred cohesiveness agents include polymers selected from polysaccharides, nucleic acids, carbohydrates, proteins, polypeptides, poly(α-hydroxy acids), poly (lactones), poly(amino acids), poly(anhydrides), poly (orthoesters), poly(anhydride-co-imides), poly (orthocarbonates), poly(α-hydroxy alkanoates), poly (dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly(ϵ-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly (vinyl alcohol), poly(vinylpyrrolidone), poly (ethyloxazoline), poly(ethylene oxide)-co-poly(propylene oxide) block copolymers, poly(ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, (β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof.

BRIEF DESCRIPTION OF THE FIGURES

The invention is described with reference to the following figures, which are presented for the purpose of illustration only and which are not intended to be limiting of the invention.

DETAILED DESCRIPTION OF THE INVENTION

Figure 1:
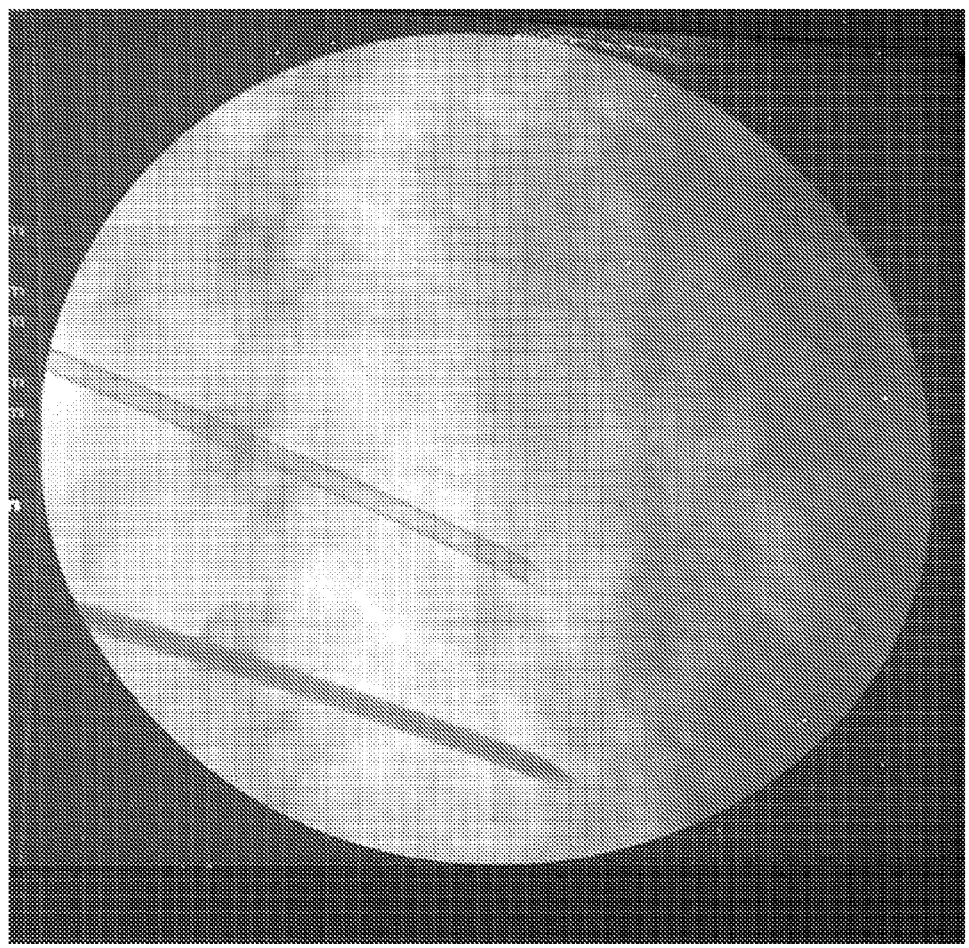
FIG. 1 is an X-ray image showing injection of the calcium phosphate material of the present invention (containing a radio-opaque agent; bottom needle) into a vertebral body of a human.
Figure 2:
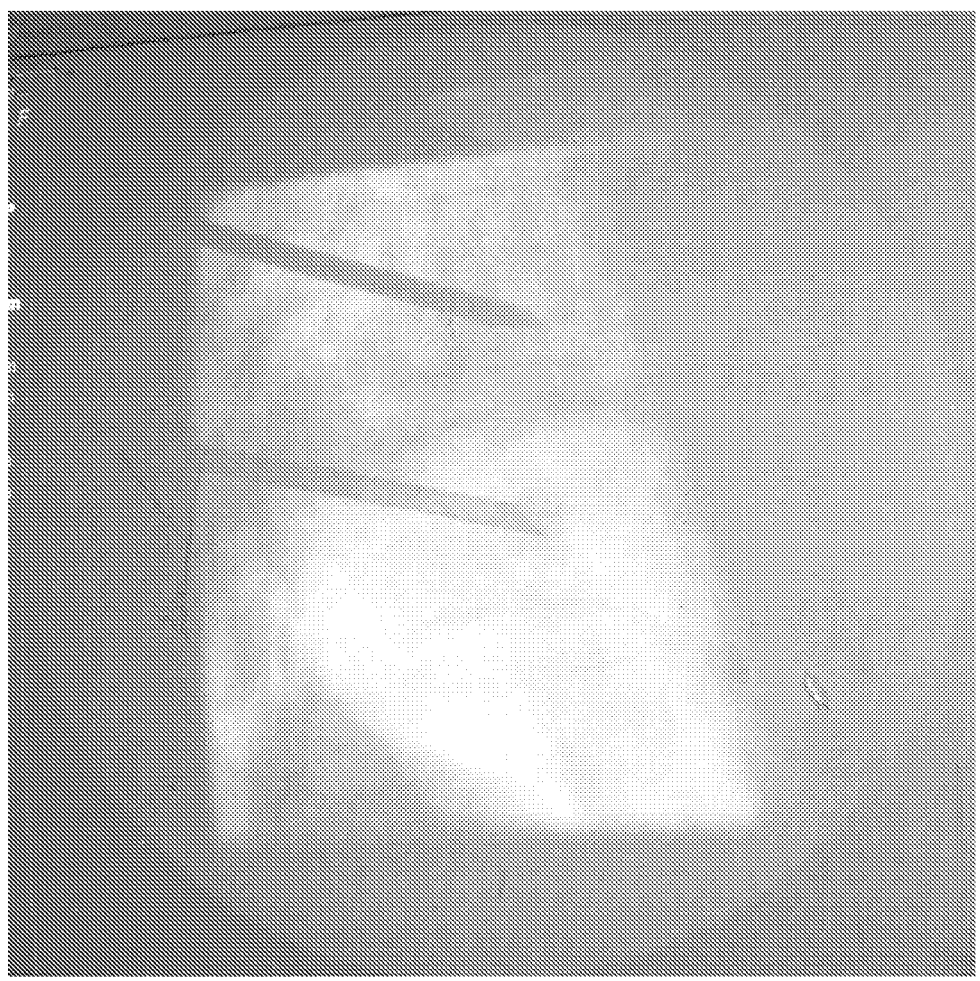
FIG. 2 is an X-ray image showing dispersal of the calcium phosphate material into the vertebral body (bottom needle) following injection.
Figure 3:
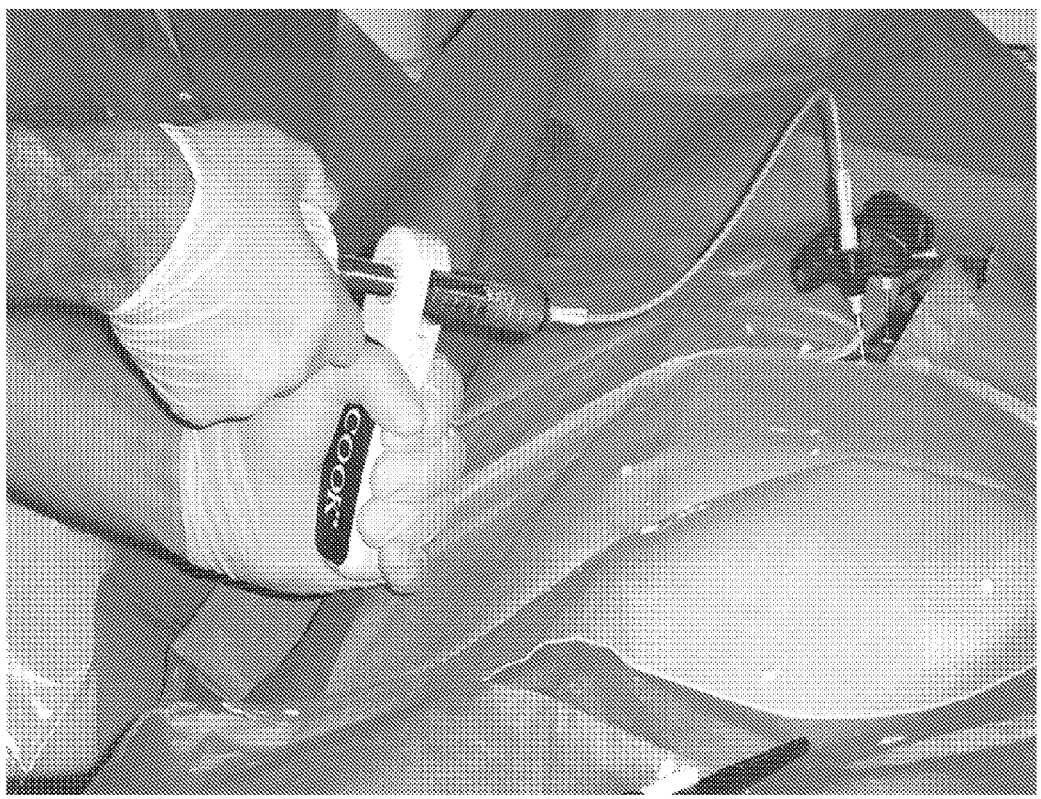
FIG. 3 is a photograph showing an external view during injection of the calcium phosphate material into the vertebra of a human.

The present invention features a biocompatible, injectable, self-setting, cohesive, bone-bonding, and remodeling calcium phosphate composite (CaP-Comp) material that can be used for vertebroplasty augmentation and kyphoplasty.

The present invention features several CaP formulations prepared by creating a chemical bond between an adhesive agent (e.g., a polymer) and a CaP material. The CaP component is not just physically mixed with the adhesive agent but is chemical bonded, e.g., by using a low temperature double decomposition wet chemistry process (see, e.g., U.S. Pat. No. 5,783,217, incorporated herein by reference), a high energy grinding process (see, e.g., U.S. Pat. Nos. 7,318,841 and 6,840,961, both of which are incorporated herein by reference), or both. In an embodiment, the CaP material is formulated as a nano-crystalline apatite (NCA) or a nano-low crystalline apatite (NLCA). These apatites are synthesized, e.g., by using the low temperature double decomposition technique discussed above.

The CaP composites of the present invention can also be prepared using one or more polymers, including, e.g., polylactic Acid (PLA), which are polymerized with the CaP by physical fixation.

The CaP composites of the present invention can also be prepared using one or more polymers, including, e.g., hydroxyethyl methacrylate (HEMA) monomers, which are used to polymerize the CaP using a chemical linkage (CaP Co-Polymerization (covalent binding)). The chemical bond may be formed through phosphate ions, which may partially replace the hydroxyl ions of apatite.

Unlike PMMA cement, the CaP composites of the present invention can be remodeled into bone. Moreover, the CaP composites of the invention do not contain volatile monomers that can be "leached" away from the composite after it has been applied to the grafting site (e.g., in vertebroplasty or kyphoplasty applications), and thus, the present CaP composites can substantially reduce the potential for significant side effects observed in PMMA applications.

Moreover, the CaP composites of the present invention can be formulated for injection (injectable), can be formulated as a formable material, which can be molded into a desired shape (e.g., formable) before implantation or at the implant site, and is biodegradable. Furthermore, the CaP composites of the invention can be used in therapeutic applications (e.g., the treatment of vertebral compression fractures) or for prophylactic applications (e.g., the augmentation of bone, such as osteoporotic bone (e.g., vertebrae)). For example, the percutaneous injection of a CaP composite of the invention into an osteoporotic vertebral body can substantially increase its fracture strength and stiffness. Moreover, injection of a CaP composite of the invention into a vertebral compression fracture can partially restore vertebral height and substantially prevent further vertebral collapse while avoiding potential problems associated with the use of PMMA.

The CaP composites of the present invention can also be used to augment the implantation of pedicle screws into osteoporotic human vertebrate. The CaP composites of the invention provide improved stability of pedicle screws in osteoporotic human vertebrae both for pullout and cyclic loading relative to other fixation compositions.

In an embodiment, the CaP composites of the invention include a biocompatible cohesiveness agent. In preferred embodiments, the cohesiveness agent includes one or more polymers selected from polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof. The cohesiveness agent can also be a poly(amino acid), in particular polyproline, poly(L-arginine), poly(L-lysine), polysarcosine, poly(L-hydroxyproline), poly(glutamic acid), poly(S-carboxymethyl-L-cysteine), and poly(aspartic acid); a homo- or co-polymer that includes one or more monomers selected from the group consisting of acrolein potassium, (meth)acrylamides, (meth)acrylic acid and salts thereof, (meth)acrylates (e.g., hydroxyl methacylate (HEMA), acrylonitrile, ethylene, ethylene glycol, ethyleneimine, ethyleneoxide, styrene sulfonate, vinyl acetate, vinyl alcohol, vinyl chloride, and vinylpyrrolidone); or a polyphenolic complexing agent (e.g., an agent selected from gallotannins, ellagitannins, taragallotannins, caffetannins, proanthocyanidins, catechin, epicatechin, chlorogenic acid, and arbutin).

Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., $\alpha$-cyclodextrin, $\beta$-cyclodextrin, $\gamma$-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. In yet another preferred embodiment, the biocompatible cohesiveness agent is present in a composition of the invention in an amount in the range of about 0.5 wt % to about 20 wt % (e.g., less than about 20 wt %, preferably less than about 10 wt %, more preferably less than about 5 wt %, and most preferably less than about 1 wt %).

In addition, the CaP composites may also include a physiologically-acceptable fluid which, when added to the dry components of the composition, produces a self-hardening paste or putty (e.g., the paste or putty hardens in about 10 minutes to about 2 hours, preferably in about 10 minutes to about 1 hour, and more preferably in about 10 minutes to about 30 minutes). In several embodiments of the invention, suitable physiologically-acceptable fluids include but are not limited to water, saline, glycerol, and phosphate buffers. In other embodiments, the fluid can be a biological fluid, e.g., any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid.

The CaP composites of the invention, once hydrated to form an paste or putty, demonstrate flow characteristics that allow them to be easily injected. Varying amounts of fluid may be added to the dry ingredients of the CaP composites to produce a paste having the desired characteristics. For example, in at least some embodiments, 0.5-2.0 cc of fluid per gram of powder is used to prepare a paste that is formable, i.e., capable of being molded and retaining its shape. In at least some embodiments, the paste is injectable, i.e., capable of passing through a 16- to 18-gauge needle. The paste can also be prepared for delivery through a catheter (e.g., a catheter having a 7-15 gauge needle, and more preferably a 7, 8, 9, 10, 11, 12, 13, 14, or 15 gauge needle). Once injected, the CaP composite retains its shape and position.

In another aspect, the CaP composite, when hydrated, produces a formable, self-hardening paste, which is moldable and cohesive when applied to an implant site in vivo, or an injectable, self-hardening composition that can be injected at the site of bone repair (e.g., a vertebral body); both the formable and the injectable compositions are capable of hardening at the implant site. Again, the compositions retain their shape and position once injected. In at least some embodiments, the paste hardens to form a CaP composite (e.g., a NCA or a NCLA) having significant compressive strength. The CaP composite may be implanted or injected in vivo in paste form or as a hardened CaP composite (e.g., molded into a desired shape, such as the shape of a bone defect to be replaced). The CaP composites of the invention can be used to repair bone, e.g., damaged bone, such as damaged vertebral bone.

According to some embodiments, the CaP composite additionally includes a biologically active agent. Biologically active agents that can be used in the compositions and methods described herein include, without limitation, an antibody, an antibiotic, a polynucleotide, a polypeptide, a protein (e.g., an osteogenic protein), an anti-cancer agent, a growth factor, and a vaccine. Osteogenic proteins include, without limitation, BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18. Anti-cancer agents include, without limitation, alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists, TNF alpha antagonists, endothelin A receptor antagonists, retinoic acid receptor agonists, immuno-modulators, hormonal agents, antihormonal agents, photodynamic agents, and tyrosine kinase inhibitors.

In another preferred embodiment, the CaP composite includes demineralized bone matrix (DBM). In a preferred embodiment, the DBM has a particle size in the range of 53-850 µm. In other embodiments, the DBM has a particle size in the range of 53-125 µm (i.e., fines) or 125-850 µm (i.e., full range DBM particles). In yet other embodiments, the DBM is provided as fibers having a fiber length in the range of about 250 µm to about 2 mm.

In other embodiments, the CaP composite includes a contrast agent (e.g., a barium apatite contrast agent; see, e.g., U.S. Patent Application Publication No. 2005/0257714, incorporated herein by reference).

In other embodiments, the CaP composites include calcium phosphate components that have a Ca/P ratio of less than 1.67. In particularly preferred embodiments, the CaP composites harden to form a composition having an overall Ca/P ratio in the range of 1.0-1.67, preferably 1.3-1.65, more preferably 1.4-1.6, and most preferably close to that of naturally occurring bone, that is in the range of 1.45 to 1.67. In a preferred embodiment, the CaP composites have a Ca/P ratio of equal to or less than about 1.5.

In yet other embodiments, the CaP composites of the invention exhibit a compressive strength of equal to or greater than about 1 or 2 MPa. In other preferred embodiments, the compressive strength is in the range of about 1 MPa to about 150 MPa (e.g., 20, 30, 40, 50, 60, 70, 80, 90, or 100 MPa). In yet other preferred embodiments, the compressive strength is 120 MPa or greater (e.g., 120 to 150 MPa).

In other embodiments, the CaP component of the CaP composites has an average crystalline domain size of less than 100 nm (e.g., in the range of between about 1 nm to about 99 nm; preferably 50 nm or less; more preferably 40, 30, 20, 10 nm or less).
The tensile strength of the crystal improves the composite's strength, and the smaller the crystal (of CaP) the better. Below a critical size particle (around 30 nanometers), a cracked crystal has the same fracture strength as a defect-free crystal.

In yet other embodiments, the CaP composite includes a radio-opaque agent. Non-limiting examples of radio-opaque agents include barium (e.g., barium carbonate and barium sulfate), iodine (e.g., methyl methacrylate, 2-(2'-iodobenzoyl)-ethyl methacrylate), lanthanum oxide, and zirconium dioxide. In other embodiments, the radio-opaque agent is present in the CaP composite in an amount of 20% or less by weight, preferably 5% or less by weight, and more preferably 1% or less by weight.

Biocompatible Cohesiveness Agents for Use in the CaP Composites of the Invention The CaP composites of the present invention may include a biocompatible cohesiveness agent. Non-limiting examples of suitable biocompatible cohesiveness agents include polymers selected from polysaccharides, nucleic acids, carbohydrates, proteins, polypeptides, poly($\alpha$-hydroxy acids), poly (lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., $\alpha$-cyclodextrin, $\beta$-cyclodextrin, $\gamma$-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. In some embodiments, the biocompatible cohesiveness agent is water-soluble. A water-soluble cohesiveness agent dissolves from the implant material shortly after its implantation in vivo, thereby introducing macroporosity into the bone implant material. This macroporosity increases the osteoconductivity of the bone implant material by enhancing the access and, consequently, the remodeling activity of the osteoclasts and osteoblasts at the implant site.

The biocompatible cohesiveness agent may be added to the CaP composites of the invention in varying amounts and at a variety of stages during the production of the powder component. The biocompatible cohesiveness agent is present in a range of about 1 to 50 weight percent. In several embodiments of the invention, the biocompatible cohesiveness agent is present in an amount less than or equal to 40 weight percent of the powder component, preferably less than or equal to 30 weight percent, more preferably less than or equal to 20 weight percent, and most preferably less than or equal to 10 weight percent. In a preferred embodiment, the biocompatible cohesiveness agent is present in an amount of about 5 weight percent.

In an embodiment of the invention, the CaP composite includes DBM. In some instances, the DBM content of the bone implant material is so high that, notwithstanding the formability and cohesiveness provided by the calcium phosphate component of the composite, a cohesiveness agent may be desirable to further augment the mechanical strength of the bone implant material during implantation. In particular embodiments, the biocompatible cohesiveness agent is present in an amount of about 10 weight percent of the powder component. In a preferred embodiment, the calcium phosphate composition includes DBM in an amount of about 40 to 50 weight percent, a calcium phosphate component in an amount of about 35 to 45 weight percent, a cohesiveness agent in an amount of about 5 to 10 weight percent, and an effervescent agent in an amount of about 5 to 10 weight percent, such that the combination of all of the components totals 100 weight percent. The biocompatible cohesiveness agent may be added to the DBM particles as a solution; for example, the cohesiveness agent can coat the DBM particles. The biocompatible cohesiveness agent may be added to the powder component of the composition, including the DBM particles and the calcium phosphate powder. Those of skill in the art will be able to determine the amount of cohesiveness agent and method of inclusion required for a given application.

Biologically Active Agents

The CaP composite of the invention can also include a biologically active agent. In general, the biologically active agent should remain active within the paste during manufacture of the CaP composite, or be capable of being subsequently activated or re-activated following manufacture of the CaP composite. Alternatively, the biologically active agent can be added at the time of implantation of the CaP composite (whether as a moldable or injectable paste or as a hardened cement) into a host or following hardening at 37° C. in an aqueous environment.

Biologically active agents that can be incorporated into the CaP composites of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the compositions of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents (e.g., cisplatin), antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and antihormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |

TABLE 1-continued

| Category | | |
|---|---|---|
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |
| | epirubicin | bleomycin sulfate (blenoxane) |
| | therarubicin | bleomycinic acid |
| | idarubicin | bleomycin A |
| | rubidazone | bleomycin B |
| | plicamycinp | mitomycin C |
| | porfiromycin | MEN-10755 (Menarini) |
| | cyanomorpholinodoxorubicin | GPX-100 (Gem Pharmaceuticals) |
| | mitoxantrone (novantrone) | |
| Antimitotic agents | paclitaxel | SB 408075 (GlaxoSmithKline) |
| | docetaxel | E7010 (Abbott) |
| | colchicine | PG-TXL (Cell Therapeutics) |
| | vinblastine | IDN 5109 (Bayer) |
| | vincristine | A 105972 (Abbott) |
| | vinorelbine | A 204197 (Abbott) |
| | vindesine | LU 223651 (BASF) |
| | dolastatin 10 (NCI) | D 24851 (ASTAMedica) |
| | rhizoxin (Fujisawa) | ER-86526 (Eisai) |
| | mivobulin (Warner-Lambert) | combretastatin A4 (BMS) |
| | cemadotin (BASF) | isohomohalichondrin-B (PharmaMar) |
| | RPR 109881A (Aventis) | ZD 6126 (AstraZeneca) |
| | TXD 258 (Aventis) | PEG-paclitaxel (Enzon) |
| | epothilone B (Novartis) | AZ10992 (Asahi) |
| | T 900607 (Tularik) | IDN-5109 (Indena) |
| | T 138067 (Tularik) | AVLB (Prescient NeuroPharma) |
| | cryptophycin 52 (Eli Lilly) | azaepothilone B (BMS) |
| | vinflunine (Fabre) | BNP-7787 (BioNumerik) |
| | auristatin PE (Teikoku Hormone) | CA-4 prodrug (OXiGENE) |
| | BMS 247550 (BMS) | dolastatin-10 (NIH) |
| | BMS 184476 (BMS) | CA-4 (OXiGENE) |
| | BMS 188797 (BMS) | |
| | taxoprexin (Protarga) | |
| Aromatase inhibitors | aminoglutethimide | exemestane |
| | letrozole | atamestane (BioMedicines) |
| | anastrazole | YM-511 (Yamanouchi) |
| | formestane | |
| Thymidylate synthase inhibitors | pemetrexed (Eli Lilly) | nolatrexed (Eximias) |
| | ZD-9331 (BTG) | CoFactor ™ (BioKeys) |
| DNA antagonists | trabectedin (PharmaMar) | mafosfamide (Baxter International) |
| | glufosfamide (Baxter International) | apaziquone (Spectrum Pharmaceuticals) |
| | albumin + 32P (Isotope Solutions) | O6 benzyl guanine (Paligent) |
| | thymectacin (NewBiotics) | |
| | edotreotide (Novartis) | |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | |
| | MS-209 (Schering AG) | biricodar dicitrate (Vertex) |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | |
| | adenocarcinoma vaccine (Biomira) | ISF-154 (Tragen) |
| | CTP-37 (AVI BioPharma) | cancer vaccine (Intercell) |
| | IRX-2 (Immuno-Rx) | norelin (Biostar) |
| | PEP-005 (Peplin Biotech) | BLP-25 (Biomira) |
| | synchrovax vaccines (CTL Immuno) | MGV (Progenics) |
| | melanoma vaccine (CTL Immuno) | β-alethine (Dovetail) |
| | p21 RAS vaccine (GemVax) | CLL therapy (Vasogen) |

TABLE 1-continued

| | | |
|---|---|---|
| Hormonal and antihormonal agents | estrogens<br>conjugated estrogens<br>ethinyl estradiol<br>chlortrianisen<br>idenestrol<br>hydroxyprogesterone caproate<br>medroxyprogesterone<br>testosterone<br>testosterone propionate;<br>fluoxymesterone<br>methyltestosterone<br>diethylstilbestrol<br>megestrol<br>tamoxifen<br>toremofine<br>dexamethasone | prednisone<br>methylprednisolone<br>prednisolone<br>aminoglutethimide<br>leuprolide<br>goserelin<br>leuporelin<br>bicalutamide<br>flutamide<br>octreotide<br>nilutamide<br>mitotane<br>P-04 (Novogen)<br>2-methoxyestradiol (EntrcMed)<br>arzoxifene (Eli Lilly) |
| Photodynamic agents | talaporfin (Light Sciences)<br>Theralux (Theratechnologies)<br>motexafin gadolinium (Pharmacyclics) | Pd-bacteriopheophorbide (Yeda)<br>lutetium texaphyrin (Pharmacyclics)<br>hypericin |
| Tyrosine Kinase Inhibitors | imatinib (Novartis)<br>leflunomide (Sugen/Pharmacia)<br>ZD1839 (AstraZeneca)<br>erlotinib (Oncogene Science)<br>canertinib (Pfizer)<br>squalamine (Genaera)<br>SU5416 (Pharmacia)<br>SU6668 (Pharmacia )<br>ZD4190 (AstraZeneca)<br>ZD6474 (AstraZeneca)<br>vatalanib (Novartis)<br>PK1166 (Novartis)<br>GW2016 (GlaxoSmithKline)<br>EKB-509 (Wyeth)<br>EKB-569 (Wyeth) | kahalide F (PharmaMar)<br>CEP-701 (Cephalon)<br>CEP-751 (Cephalon)<br>MLN518 (Millenium)<br>PKC412 (Novartis)<br>phenoxodiol ( )<br>trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |

The CaP composites can also include medicinal agents, e.g., antibiotics, such as aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances that inhibit an enzymatic reaction. Examples of enzyme inhibitors that can be included in the CaP composites of the invention include, e.g., edrophonium chloride, N-methylphysostigmine, neostigmine bromide, physostigmine sulfate, tacrine, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthen, papaverine, indomethacin, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines that can be included in CaP composites of the invention include, e.g., pyrilamine, chlorpheniramine, and tetrahydrazoline, among others.

Anti-inflammatory agents that can be included in CaP composites of the invention include, e.g., corticosteroids, nonsteroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants that can be included in CaP composites of the invention include, e.g., mephenesin, methocarbomal, cyclobenzaprine hydrochloride, trihexylphenidyl hydrochloride, levodopa/carbidopa, and biperiden.

Anti-spasmodics that can be included in CaP composites of the invention include, e.g., atropine, scopolamine, oxyphenonium, and papaverine.

Analgesics that can be included in CaP composites of the invention include, e.g., aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, nor-binaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents that can be included in CaP composites of the invention include, e.g., sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins, which are art recognized as a class of naturally occurring chemically related, long-chain hydroxy fatty acids that have a variety of biological effects, can also be included in CaP composites of the invention.

Anti-depressants are substances capable of preventing or relieving depression. Examples of anti-depressants that can be included in CaP composites of the invention include, e.g., imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors that can be included in CaP composites of the invention include, without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, transforming growth factors (beta), including beta-1, beta-2, beta-3, inhibin, and activin; and bone morphogenetic proteins such as OP-1, BMP-2 and BMP-7.

Hormones that can be included in CaP composites of the invention include, e.g., estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronine, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, which are also used as immunosuppressants and anti-inflammatories, can be included in CaP composites of the invention.

Osteogenic Proteins

The biologically active agent is desirably selected from the family of proteins known as the transforming growth factors-beta (TGF-β) superfamily of proteins, which includes the activins, inhibins, and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-3b, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO 91/18098; and BMP-9, disclosed in PCT publication WO 93/00432, BMP-10, disclosed in PCT application WO 94/26893; BMP-11, disclosed in PCT application WO 94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other BMPs include BMP-17 and BMP-18.

Other TGF-β proteins that may be useful as the active agent in the CaP composites of the invention include, e.g., Vgr-2, Jones et al., *Mol. Endocrinol.* 6:1961 (1992), and any of the growth and differentiation factors (GDFs), including those described in PCT applications WO 94/15965; WO 94/15949; WO 95/01801; WO 95/01802; WO 94/21681; WO 94/15966; WO 95/10539; WO 96/01845; WO 96/02559 and others. Also useful in the invention may be BIP, disclosed in WO 94/01557; HP00269, disclosed in JP Publication number: 7-250688; and MP52, disclosed in PCT application WO 93/16099. The disclosures of all of the above applications are incorporated herein by reference. A subset of BMPs which are presently preferred for use in the invention include BMP-2, BMP-4, BMP-5, BMP-6, BMP-7, BMP-10, BMP-12, BMP-13, BMP-14, and MP52. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, or LIM protein, among others.

The biologically active agent may be recombinantly produced, or purified from a protein composition. The active agent, if a TGF-β, such as a BMP, or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is hereby incorporated herein by reference.

The biologically active agent may further include additional agents such as the Hedgehog, Frazzled, Chordin, Noggin, Cerberus and Follistatin proteins. These families of proteins are generally described in Sasai et al., Cell 79:779-790 (1994) (Chordin); PCT Patent Publication WO 94/05800 (Noggin); and Fukui et at, *Devel. Biol.* 159:131 (1993) (Follistatin). Hedgehog proteins are described in WO 96/16668; WO 96/17924; and WO 95/18856. The Frazzled family of proteins is a recently discovered family of proteins with high homology to the extracellular binding domain of the receptor protein family known as Frizzled. The Frizzled family of genes and proteins is described in Wang et al., *J. Biol. Chem.* 271:4468-4476 (1996). The active agent may also include other soluble receptors, such as the truncated soluble receptors disclosed in PCT patent publication WO 95/07982. From the teaching of WO 95/07982, one skilled in the art will recognize that truncated soluble receptors can be prepared for numerous other receptor proteins. The above publications are hereby incorporated by reference herein. The amount of osteogenic protein effective to stimulate increased osteogenic activity of present or infiltrating progenitor or other cells will depend upon the size and nature of the defect being treated, as well as the carrier being employed.

Generally, the biologically active agent is included in the CaP composite in an amount sufficient to treat or ameliorate a bone defect or injury (e.g., a vertebral body defect or injury), when the CaP composite is being used in connection with bone regeneration. By "an amount sufficient" is meant the amount of a biologically active agent required in the CaP composite to promote a clinically relevant effect. A sufficient amount of a biologically active compound used to practice the present invention for therapeutic purposes varies depending upon the manner of administration, the age, body weight, and general health of the patient. Ultimately, the prescribers will decide the appropriate amount and dosage regimen. The appropriate amounts for any monotherapy or combination therapy described herein can be determined from animal models, in vitro assays, and/or clinical studies.

By way of example, the amount of a biologically active agent included in the CaP composite can be in the range of from about 0.1 ng to about 10.0 g per kg; preferably about 1.0 µg to about 1000.0 mg per kg; most preferably about 10.0 µg to about 10.0 mg per kg.

Biologically active agents can be introduced into the CaP composites of the invention during or after its formation. Agents may conveniently be mixed into the compositions prior to setting. Alternatively, the CaP composite may be shaped and hardened and then exposed to the therapeutic agent in solution. This particular approach is particularly well suited for proteins, which are known to have an affinity for apatitic materials. A buffer solution containing the biologically active agent may be employed, instead of water, as the aqueous solution in which the self-hardening paste is, for example, irrigated prior to implantation. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Demineralized Bone Matrix

In a preferred embodiment, the biologically active agent is DBM. DBM is an organic, osteoinductive material most commonly obtained from long bone chips demineralized by acid treatment. The acid treatment dissolves inorganic mineral components and acid-soluble proteins in the bone, leaving behind a collagen matrix as well as acid-insoluble proteins and growth factors (see, e.g., Glowacki et al. (1985) *Clin. Plant. Surg.* 12(2):233-241; Covey et al. (1989) *Orthop. Rev.* 17(8):857-863). Among the residual acid-insoluble proteins and growth factors are osteoinductive factors, such as bone morphogenic proteins (BMPs) and transforming growth factors (TGFs). Thus, DBM is osteoinductive, fully resorbable, and, when used in combination with the calcium phosphate component of the CaP composites described herein, yields bone implant materials that are highly biocompatible because they closely mimic the chemical composition of natural bone. Advantageously, DBM costs less than many other available organic bone composition additives, such as isolated BMPs.

The DBM employed in the CaP composites of the invention is preferably derived from autogenic or allogenic sources. As discussed above, DBM may be obtained by acid treatment of long bone chips, a process well known to those of ordinary skill in the art. Alternatively, commercially available DBM may be used (e.g., DBM available from Allosource, American Red Cross, Musculoskeletal Transplant Foundation, Regeneration Technologies, Inc., and Osteotech, Inc.).

In at least some embodiments, the DBM in the bone implant materials is present in an amount between about 10 and about 70 weight percent of the powder component. In particular embodiments, the DBM is present in an amount equal to about 60 weight percent of the powder component. In other embodiments, the DBM is present in an amount between about 1 and about 50 weight percent of the powder component. In still other embodiments, the DBM is present in an amount less than or equal to about 20 weight percent of the powder component. Preferably, the DBM is present in an amount less than or equal to about 15 weight percent of the powder component.

The amount of DBM in a given composition will vary depending upon the amount of the biocompatible cohesiveness agent, as well as the intended use and desired characteristics of the CaP composite. In particular embodiments, the cohesiveness agent and the DBM are present in the CaP composite in a ratio of about 1:1 (e.g., in an amount in the range of about 0.5 and about 20 weight percent of the powder component), preferably about 1:5, more preferably about 1:10, and most preferably about 1:20. In preferred embodiments, the cohesiveness agent is present in an amount of about 5 weight percent or less.

Those of skill in the art will be able to determine the amount of biologically agent (e.g., DBM), calcium phosphate, cohesiveness agent, and other agents required for particular applications. For example, a preferred calcium phosphate powder composition includes about 15 weight percent DBM and about 85 weight percent calcium phosphate powder having between about 1 to about 10 weight percent cohesiveness agent and effervescent agent. Another preferred calcium phosphate powder composition includes about 45 weight percent DBM, about 45 weight percent calcium phosphate powder and about 10 weight percent biocompatible cohesiveness agent.

The DBM particles may be of various sizes and physical forms. As with the amount of DBM, the size and form of the DBM particles will vary depending upon the intended use of the bone implant material. In some embodiments, the DBM particles have a longest dimension measuring between about 35 µm and about 850 µm and may further have an aspect ratio of less than about 5. In other embodiments, the DBM particles are fibrous in nature. In some embodiments, these DBM fibers have a length between about 50 µm and about 3 mm. In other embodiments, the DBM fibers have a length between about 250 µm and about 2 mm. In some embodiments, the aspect ratio of these DBM fibers is greater than 4. In other embodiments, the aspect ratio of these DBM fibers is greater than 10. The DBM fibers may be needle-like, having an average width to average thickness ratio of less than 5. Methods of producing DBM particles of varying sizes will be well-known to those of skill in the art and are disclosed, for example, in U.S. Patent Application Publication No. 2004/0097612, which is incorporated herein by reference. Of note, the needle-like, fibrous DBM obtained from long bone chips or shavings, as opposed to DBM obtained from ground bone, provide increased cohesiveness when incorporated into the calcium phosphate compositions of the present invention.

EXAMPLES

The following examples are to illustrate the invention. They are not meant to limit the invention in any way.

Example I

Preparation of Nano Crystalline Apatite (NCA) with No Crystal Growth Inhibitor

Add 100 g of $Na_2HPO_4, 7H_2O$ to 1000 ml of distilled water to prepare a solution of 0.37 M (Solution 1). Add 35 g of $Ca(NO_3)_2, 4H_2O$ to 300 ml of distilled water to prepare a solution of 0.49 M (Solution 2).

Add rapidly solution 2 to solution 1, stir vigorously for 5 minutes at room temperature to produce slurry. After filtration, washing and freeze-drying (by adding liquid nitrogen into the wet cake), NCA nano-particle is obtained. Activate NCA powder (at 120° C. during 2 hours) by removing excessive moisture (about 3 to 10%).

In this example the crystallinity index of NCA produced is estimated (by comparing with hydroxyapatite) to be around 60% with the nano-size crystal range: 30-80 nm.

Example 2

Preparation of Nano Low Crystalline Apatite (NLCA) with One Crystal Growth Inhibitor ($CO_3^{2-}$ Ions)

Add 100 g of $Na_2HPO_4$, $7H_2O$ to 1000 ml of distilled water to prepare a solution of 0.37 M. Once dissolved, add 40 g of $NaHCO_3$ and stir to dissolve (Solution 1).

Add 35 g of $Ca(NO_3)_2$, $4H_2O$ to 300 ml of distilled water to prepare a solution of 0.49 M (Solution 2).

Add rapidly solution 2 to solution 1, stir vigorously for 5 minutes at room temperature to produce slurry. After filtration, washing and freeze-drying (by adding liquid nitrogen into the wet cake), NLCA nano-particle is obtained. Activate NLCA powder (at 120° C. during 2 hours) by removing excessive moisture (about 3 to 10%).

In this example the crystallinity index of NLCA produced is estimated (by comparing with hydroxyapatite) to be around 50% with nano-size crystal range: 30-50

Example 3

Preparation of Nano Low Crystalline Apatite (NLCA) with Two Crystal Growth Inhibitors ($CO_3^{2-}$ and $P_2O_7^{4-}$ Ions)

Add 100 g of $Na_2HPO_4$, $7H_2O$ to 1000 ml of distilled water to prepare a solution of 0.37 M. Once dissolved, add 40 g of $NaHCO_3$ and stir to dissolve. Once all dissolved, add 0.5. $Na_4P_2O_7$, $10H_2O$ and stir to dissolve (Solution 1).

Add 35 g of $Ca(NO_3)_2$, $4H_2O$ to 300 ml of distilled water to prepare a solution of 0.49 M (Solution 2).

Add rapidly solution 2 to solution 1, stir vigorously for 5 minutes at room temperature to produce slurry. After filtration, washing and freeze-drying (by adding liquid nitrogen into the wet cake), NLCA nano-particle is obtained. Activate NLCA powder (at 120° C. during 2 hours) by removing excessive moisture (about 3 to 10%).

In this example the crystallinity index of NLCA produced is estimated (by comparing with hydroxyapatite) to be around 40% with nano-size crystal range: 30-50 nm.

Example 4

Preparation of Nano Low Crystalline Apatite (NLCA) with Three Crystal Growth Inhibitors ($CO_3^{2-}$, $P_2O_7^{4-}$ and $Mg^{2+}$ Ions)

Add 100 g of $Na_2HPO_4$, $7H_2O$ to 1000 ml of distilled water to prepare a solution of 0.37 M. Once dissolved, add 40 g of $NaHCO_3$ and stir to dissolve. Once all dissolved, add 0.5. $Na_4P_2O_7$, $10H_2O$ and stir to dissolve (Solution 1).

Add 35 g of $Ca(NO_3)_2$, $4H_2O$ to 300 ml of distilled water to prepare a solution of 0.49 M. Once dissolved, add 0.5 g $MgCl_2$, $6H_2O$ (Solution 2).

Add rapidly solution 2 to solution 1, stir vigorously for 5 minutes at room temperature to produce slurry. After filtration, washing and freeze-drying (by adding liquid nitrogen into the wet cake), NLCA nano-particle is obtained. Activate NLCA powder (at 120° C. during 2 hours) by removing excessive moisture (about 3 to 10%).

In this example the crystallinity index of NLCA produced is estimated (by comparing with hydroxyapatite) to be around 40% with nano-size crystal range: 30-50 nm.

Example 5

Co-Polymerization (Physical Fixation of CaP-Polymers)

Prepare apatite (NCA and/or NLCA) powder according to Example 1, 2, 3 or 4.

Dissolve about 25 g PLA (Polylactic Acid) powder in a solvent (acetone for example) in order to obtain a homogenous liquid.

Mix apatite powder with PLA solution (with the ratio of PLA about 25% w/w). Stir vigorously (at room temperature) during 2 h in order to prepare emulsion. Vacuum dry the emulsion during 2 h at 100° C. in order to remove the residual solvent (by evaporation) and produce a dry powder.

Ground the powder in the high energy dry ball mill process for 1 to 5 hours in order to densify the material. The residence time in the high energy grinding process will first reduce the particle size and then partially amorphize the material. By varying the residence time, materials with different mechanical performance can be prepared.

Example 6

Co-Polymerization (Chemical Linkage, Covalent Binding) of CaP Materials

Prepare apatite (NCA and/or NLCA) powder according to Example 1, 2, 3 or 4.

Prepare a homogenous powder by mixing about 20 g apatite powder with 1.2 g of Benzoyl Peroxide powder (Powder 1).

Add on 20 g Hydroxyethyl Methacrylate (HEMA), about 0.8 ml Dimethyl-ρ-Toluidine and stir to prepare a solution (Solution 1).

Add all of solution 1 to powder 1, at room temperature and stir vigorously to obtain emulsion of Apatite-HEMA. The emulsion is vacuum dried at 80° C., for 4 h to remove all residual solvent by evaporation process.

The irreversible link between the ethylenic bond of Apatite-HEMA produces a hydrophilic material that forms a colloid-like material when mixed with hydration media (for example, water or any other pharmaceutically acceptable liquid described herein).

By grinding the powder in the dry ball mill at various conditions (media-powder ratio, residence time, RPM) and compacting/densification of powder, various self-setting CaP-polymeric cements is produced.

Example 7

Imaging Capability of CaP Paste Injected into Adult Cadaveric Vertebral

CaP material made according to the recipe developed previously (see, e.g., U.S. Pat. No. 7,318,841, incorporated herein by reference).

CaP cement powder was mixed with 5% (w/w) Sodium Alginate powder.

CaP material was injected into two adult cadaveric vertebral bodies to assess the imaging capabilities (radiopacity) of paste under fluoroscopy.

The hydration media was physiological saline with 20% Renografin-60 (organically bond Iodine) solution in order to increase radiopacity capacity.

Two Adult cadaveric spines were used. Each vertebral body was injected (through 12G long needle) with about 4 cc CaP cement through two pedicles (with in total 6 levels of spine). Each pedicle was injected separately.

Injection process conducted successfully with clear visualization of CaP-Alginate paste through vertebral bodies.

Example 8

CaP Matrix with Cohesiveness Agent (CA)

CaP material made according to the recipe developed previously (see, e.g., U.S. Pat. No. 7,318,841, incorporated herein by reference).

The CA used is sodium alginate with the ratio of 1 to 20 w/w %.

CaP-Alginate (2 w/w %) was previously injected into sheep lumbar (L3-L4) vertebrae (after conducting the defect). At 6 month time point, no signs of acute or chronic inflammation observed. Histology analysis confirmed remodeling and osseointegration on both stained sections and microradiographs. Larger quantity of new bone was present and organized in a concentric lamellar pattern.

Example 9

CaP Matrix with Osteoinductive Agents (OI)

CaP material made according to the recipe developed previously (see, e.g., U.S. Pat. No. 7,318,841, incorporated herein by reference).

The OI used is demineralized bone matrix (DBM) with various ratios, e.g., 1:1 calcium phosphate material (CaP): DBM; 2:1 (CaP:DBM); 3:1 (CaP:DBM); 4:1 (CaP:DBM); 5:1 (CaP:DBM); and 10:1 (CaP:DBM).

The CaP/DBM composites are to be injected into sheep lumbar (L3-L4) vertebrae (after conducting the defect). At 6 month time point, the injection site will be examined for signs of acute or chronic inflammation Histology analysis, using, e.g., stained sections and microradiographs, will be undertaken to confirm that remodeling and osseointegration has occurred.

Example 10

CaP Matrix with Medicinal Agents (MA)

CaP material made according to the recipe developed previously (see, e.g., U.S. Pat. No. 7,318,841, incorporated herein by reference).

The MA used is different kinds of antibiotics with various ratios (e.g., 2:1 (CaP:MA); 10:1 (CaP:MA); 20:1 (CaP:MA); and 50:1 (CaP:MA).

Three common medicinal agents tested (Gentamicin, Tobramycin and Vancomycin) did not adversely affect the performance (e.g., hardening time and compressive strength) of the CaP composite.

Additional work with Tobramycin showed that at a dosage greater than 100 mg/gm hardening was inhibited. At 60 mg/gm or less CaP-Tobramycin hardened normally.

Example 11

Combination Composite

CaP material made according to the recipe developed previously (see, e.g., U.S. Pat. No. 7,318,841, incorporated herein by reference).

In these engineered formulation various combination materials using different CaP matrix, CAs, OIs, and MAs are proposed.

Bioresorbable, biocompatible, injectable, self-setting, high-strength, bone-bonding calcium phosphate combination bone graft materials (i.e., CaP composites) for the treatment of osteoporotic bone is produced.

Example 12

Multiple formulations of CaP composites were tested for applicability for Vertebroplasty in a human cadaver model. CaP composites were prepared by mixing dry powders of a high strength, fast setting calcium phosphate and carboxylmethyl cellulose (CMC). The dry powders were hydrated and mixed with an iodine based contrast agent, ISOVUE (Bracco Diagnostics), until a smooth paste was formed. Percent CMC, CMC molecular weight, and hydration volume were varied to create different CPC formulations.

Each CaP CPC formulation was loaded into a delivery syringe attached to an 11 gauge vertebroplasty needle and delivered under fluoroscopy into a separate vertebral body. CaP composites were evaluated for ease of visualization, ease of delivery, and dispersion. A PMMA designed for vertebroplasty use (Cook) was used as a reference.

All CaP composites were easily visualized under fluoroscopy. Higher concentrations of CMC in the CaP composite, the use of high molecular weight CMC, and a lower hydration volume each contributed to decreased dispersion and leakage of the CaP composite material from the injection site and each was also associated with higher delivery forces. CaP composites prepared with 10% high molecular weight CMC and hydrated at hydrant to powder ratios of 0.5 to 0.6 mL/g did not exhibit any dispersion or leakage issues and were easily injected with the standard delivery devices.

Example 13

Vertebroplasty involves injecting the bone cement of the present invention into small holes in weakened vertebrae to strengthen the spinal bones making them less likely to fracture again and providing pain relief. Using image-guidance, a hollow needle called a trocar is passed through the skin into the spinal bone and the bone cement of the present invention is then injected into the vertebra.

Kyphoplasty is a minimally invasive spinal surgery procedure used to treat painful, progressive vertebral compression fractures (VCFs). A VCF is a fracture in the body of a vertebra, which causes it to collapse. In turn, this causes the spinal column above it to develop an abnormal forward curve. VCFs may be caused by osteoporosis (an age-related softening of the bones) or by the spread of tumor to the vertebral body. Certain forms of cancer can also weaken bone and cause the same problems.

In kyphoplasty, a balloon is first inserted through the tube and into the vertebral body of a fractured vertebra where it is inflated to restore the height and shape of the vertebral body. The balloon is then removed. This is followed by injection of a bone cement of the present invention into the cavity formed by the balloon to strengthen the vertebra. The procedure may be performed with the patient lying face down on the operating room table and under intravenous sedation. X-ray machines (e.g., one, two, or more used together) can be used to show the collapsed bones. The surgeon makes two small (less than 3 mm) incisions in the back. A tube is inserted into the center of the vertebral body to the site of the fractured bone. The balloon tamp is then inserted down the tube and inflated. This pushes the bone back to its normal height and shape. Inflation of the balloon creates a cavity in the vertebral body, which the surgeon fills with the bone cement of the present invention. When the cement hardens, the tubes are removed. The incisions can be closed with surgical stitches.

It is recommended that kyphoplasty be performed soon after a VCF happens to best restore vertebral body height and size. After kyphoplasty, severe osteoporosis may cause other fractures at other levels of the spine. Patients can also take bone-strengthening medications during treatment. If more vertebrae collapse, kyphoplasty in conjunction with the bone cement of the present invention can be used at those other levels. Kyphoplasty tends to help prevent additional fractures by keeping the spine aligned in its native upright position.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated to be incorporated by reference in their entirety.

What is claimed is:

1. A method for performing vertebroplasty on a vertebral body comprising:
  a) injecting a flowable bone cement into at least one said vertebral body, said flowable bone cement comprising a nanocrystalline apatitic calcium phosphate, a radio-opaque agent, and a pharmaceutically acceptable fluid in an amount sufficient to produce said flowable bone cement, wherein said nanocrystalline apatitic calcium phosphate comprises crystals having a domain size within the range of 30-80 nm; and
  b) allowing said flowable bone cement to harden, wherein said flowable bone cement, when hardened, has a compressive strength of 1 MPa or greater and is resorbable in vivo.

2. The method of claim 1, wherein said flowable bone cement further comprises at least one agent that promotes bone growth or inhibits bone resorption, one or more crystal growth inhibitors, demineralized bone matrix, benzoyl peroxide powder, or hydroxyethyl methacrylate (HEMA).

3. The method of claim 2, wherein said flowable bone cement further comprises HEMA.

4. The method of claim 1, wherein the pharmaceutically acceptable fluid is selected from water, saline, a phosphate buffer, a biological fluid, in particular, blood or a fluid that includes blood components, and glycerol.

5. The method of claim 1, wherein said vertebral body is in a human or non-human mammal.

6. The method of claim 1 further comprising injecting said flowable bone cement into two or more vertebral bodies.

7. The method of claim 1, wherein said vertebral body comprises fractured or osteoporotic bone.

8. The method of claim 1, wherein said nanocrystalline apatitic calcium phosphate has a crystallinity index value of less than 60% relative to hydroxyapatite.

9. The method of claim 1, wherein said flowable calcium phosphate cement further comprises a cohesiveness agent, an osteogenic agent, or a medicinal agent.

10. The method of claim 9, wherein said cohesiveness agent is selected from the group consisting of:
  a) one or more polymers selected from polysaccharides, nucleic acids, carbohydrates, proteins, polypeptides, poly(a-hydroxy acids), poly(lactones), poly(amino acids), poly(anhydrides), poly(orthoesters), poly(anhydride-co-imides), poly(orthocarbonates), poly(a-hydroxy alkanoates), poly(dioxanones), poly(phosphoesters), poly(L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate)polyamide, and copolymers thereof;
  b) a homo- or co-polymer having one or more monomers selected from the group consisting of acrolein potassium, (meth)acrylamides, (meth)acrylic acid and salts thereof, (meth)acrylates, acrylonitrile, ethylene, ethylene glycol, ethyleneimine, ethyleneoxide, styrene sulfonate, vinyl acetate, vinyl alcohol, vinyl chloride, and vinylpyrrolidone);
  c) a polyphenolic complexing agent selected from gallotannins, ellagitannins, taragallotannins, caffetannins, proanthocyanidins, catechin, epicatechin, chlorogenic acid, and arbutin; and
  d) an agent selected from alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, in particular, carboxymethyl cellulose, a glucosamine, a proteoglycan, a starch, lactic acid, a pluronic, sodium glycerophosphate, collagen, glycogen, a keratin, silk, and mixtures thereof;
  said osteogenic agent is selected from the group consisting of transforming growth factors-beta (TGF-$\beta$), activins, inhibins, and bone morphogenetic proteins (BMPs); and
  said medicinal agent is selected from the group consisting of antibiotics, enzyme inhibitors, antihistamines, anti-inflammatory agents, muscle relaxants, anti-spasmodics, analgesics, prostaglandins, anti-depressants, trophic factors, and hormones.

11. The method of claim 1, comprising injecting said flowable bone cement into said vertebral body using a needle having a size of 16 gauge or less.

12. The method of claim 11, wherein said needle is an 11 gauge needle.

13. The method of claim 1, further comprising creating a cavity in said vertebral body and injecting said flowable bone cement into said cavity.

14. The method of claim 1, wherein said nanocrystalline apatitic calcium phosphate is selected from amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof.

15. The method of claim 1, wherein said nanocrystalline apatitic calcium phosphate comprises crystals having a domain size within the range of 30-50 nm.

16. The method of claim 1, wherein said nanocrystalline apatitic calcium phosphate consists of crystals having a domain size within the range of 30-80 nm.

* * * * *